United States Patent [19]

Linial et al.

[11] Patent Number: 4,665,928

[45] Date of Patent: May 19, 1987

[54] RANGE OF MOTION MEASURING AND DISPLAYING DEVICE

[75] Inventors: Andrew V. Linial, Daytona; John M. Hoyt, Ormund Beach; Dennis D. Luban, S. Daytona; James M. Cullers, Ormund Beach, all of Fla.

[73] Assignee: Orthotronics, Inc., Daytona Beach, Fla.

[21] Appl. No.: 748,230

[22] Filed: Jun. 24, 1985

Related U.S. Application Data

[63] Continuation-in-part of Ser. No. 521,925, Aug. 10, 1983, abandoned.

[51] Int. Cl.$^4$ .............................................. A61B 5/10
[52] U.S. Cl. .............................. 128/782; 272/DIG. 5
[58] Field of Search ........... 128/782; 33/1 PT, 174 B; 272/DIG. 5, DIG. 6; 73/379, 380, 381

[56] References Cited

U.S. PATENT DOCUMENTS

| | | | |
|---|---|---|---|
| 4,099,713 | 7/1978 | Spector | 272/DIG. 5 |
| 4,112,926 | 9/1978 | Schulman et al. | 128/782 |
| 4,136,955 | 1/1979 | Aeschlimann et al. | 356/152 |
| 4,408,613 | 10/1983 | Relyen | 272/DIG. 5 |
| 4,409,992 | 10/1983 | Sidorenko et al. | 128/782 |
| 4,423,630 | 1/1984 | Morrison | 272/DIG. 5 |
| 4,436,099 | 3/1984 | Raftopovlos | 128/782 |

FOREIGN PATENT DOCUMENTS

8101506 6/1981 PCT Int'l Appl. ................. 128/782

*Primary Examiner*—Edward M. Coven
*Attorney, Agent, or Firm*—Sherman and Shalloway

[57] ABSTRACT

An improved range of motion measuring and displaying device is disclosed herein which includes a modular housing containing a micro-computer and associated circuitry as well as input controls, display and printout facilities, input and output cord connections and a software receiving area which is provided so as to detachably connect to the modular housing diverse programs enabling diverse modes of operation of the invention. One of the cord connections is provided for attachment thereto of the cord of an electronic goniometer which has been designed specifically to interface with the modular housing. The electronic goniometer is of the variable resistance type and outputs voltages interpretable by the micro-computer which voltages are indicative of a rotation of the electronic goniometer with respect to an original vertical position. In one embodiment of the present invention, the modular housing has cord connections for a plurality of such electronic goniometers which may be used simultaneously in the operation of the present invention so as to determine the range of motion of a plurality of joints with respect to one another, such as separate vertabral joints of the spinal column. The present invention is usable to measure the range of motion of the various joints of the human body in any desired sequence and includes a separate mode enabling the performance of sets and repetitions of various exercises with the various body joints with the micro-computer monitoring such exercises.

24 Claims, 12 Drawing Figures

```
***  PHYSICAL THERAPY  ***
KNEE
037 DEGREES FLEXATION
ACTIVE RANGE OF MOTION
02 SETS        02 REPS

***  PHYSICAL THERAPY  ***
INDEX FINGER
MP
063
PASSIVE RANGE OF MOTION
03 SETS        03 REPS
```

Fig. 9

```
DATE  03/21/85
------------------------
PATIENT NAME, NO.: 123456
SMITH
SIGNED
------------------------

ACTIVE RANGE OF MOTION

PENDULUM A IS:    AT THORACIC 12
PENDULUM B IS:    AT THORACIC 6

FLEXION
A IS:  0 DEGREES
B IS:  0 DEGREES

EXTENSION
A IS:  0 DEGREES
B IS:  0 DEGREES

RIGHT LATERAL BEND
A IS:  0 DEGREES
B IS:  0 DEGREES

LEFT LATERAL BEND
A IS:  0 DEGREES
B IS:  0 DEGREES

RIGHT ROTATION
A IS:  0 DEGREES
B IS:  0 DEGREES

LEFT ROTATION
A IS:  0 DEGREES
B IS:  0 DEGREES
```

Fig. 11

RANGE OF MOTION MEASURING AND DISPLAYING DEVICE

BACKGROUND OF THE INVENTION

This application is a Continuation-In-Part of application Ser. No. 521,925 filed Aug. 10, 1983, now abandoned.

Individuals may experience reduced ranges of motion between the various joints of their body as a result of physical injury or other infirmity. Changes in the range of motion including increases and decreases thereof are relevant to the evaluation of recovery or disability and therefore accurate measurements of the range of motion of the various joints of the body are critical.

In the prior art, the range of motion of the various joints of the body was measured through the use of a manually operated goniometer merely consisting of two straight members, for example, metal rulers, pivoted together at the center of a graduated semi-circular protractor-type device. Such a goniometer was used through the manual placement thereof on a joint of the body with one of the rulers parallel with one bone of the joint and the other of the rulers parallel to the other bone of the joint. The operator of this goniometer would then move the moveable ruler in correspondence with movement of one of the bones with respect to the other bone through the maximum range of motion thereof as permitted by the patient's particular condition. Thus, the location of the moveable ruler with respect to the angular scale of the goniometer would yield a reading of the actual range of motion. Of course, this method and means for measuring the range of motion has severe limitations in accuracy and ease of use since improper alignment of the device or inadvertant movements of the operator's hand may result in angular readings having an error of 10° or more. Since a severe accident may reduce the range of motion in a particular joint by less than 10%, the above described margin of error for the prior art goniometer is within the range of loss of motion and is therefore a device having sufficient inaccuracy so as to render it virtually unusable as an accurate medical measuring tool.

In 1977, the American Medical Association published a publication entitled "Guides to the Evaluation of Permanent Impairment" as a tool to assist in evaluating or rating permanent disabilities related to changes in range of motion. Therein, a method is set forth in determining the present range of motion which method is believed to have a shortcoming by failing to adequately explain how a neutral point is determined. Further, for example, on page 42 of the AMA publication, a method for measuring ranges of motion in the cervical spinal region are described which are extremely subjective in nature both in the measuring technique and evaluation thereof.

Therefore, in light of the AMA publication and the shortcomings of the prior art goniometer as explained hereinabove, a need has developed for a measuring instrument able to measure the range of motion of the various joints of the body to within an error of 1% or less. Such an increase in accuracy would be beneficial not only for the treating and evaluating doctors but would be of equal important to other medical fields such as physical therapy, occupational therapy and rehabilitation, wherein the therapist places the patient on an exercise program requiring a predetermined number of repetitions of movements of a joint at a minimum predetermined range of motion. Such a device would also have great commercial applications in the field of sports medicine, evaluation of insurance claims, in industrial hiring situations, in military personnel, as well as in arbitration and litigation proceedings.

With these goals in mind, the predecessor to the present invention was invented and disclosed in the above listed parent U.S. application Ser. No. 521,925 filed Aug. 10, 1983, now abandoned. Therein, a range of motion measuring device was disclosed with the goal of increasing the accuracy in the measurement of the range of movement of the various joints of the body. As disclosed therein, one embodiment included a goniometer consisting of a movement sensitive gear system used in conjunction with an infrared light system to sense movements, react to those movements and measure the movements with increased accuracy. In a further embodiment disclosed therein, a shaft encoder was used in determining the absolute angle with this device having a pendulum attached to the shaft which remained vertical while the housing rotated along with the moving limb of the joint being measured. In a further aspect of the invention disclosed in the parent application, a relatively basic potentiometer arrangement was employed. In each of the above described embodiments, a microcomputer accepted encoded data from the goniometer and calculated an absolute difference between the current position and the beginning position called the "gravity reference position". The absolute difference of this calculated figure was then displayed on a digital readout and preserved in the internal memory of the micro-computer for subsequent printing upon a paper roll as desired.

In the invention described in the above referenced patent application, the embodiment utilizing a potentiometer as the goniometer utilized a standard off the shelf potentiometer (FIG. 4) having an elongated rotatable shaft to which was rigidly connected a pendulum having a weight. Thus, as the casing thereof rotated, the weight would tend to maintain a vertical position with respect to the center of the earth due to gravity forces which would then rotate the potentiometer shaft yielding a voltage output therefrom which could be interpreted so as to define the range of motion accrued. This potentiometer operated goniometer was simple in construction but was not specifically designed for the use to which it was put and therefore had severe drawbacks. Firstly, the potentiometer was not designed to rotate based upon the movement of a housing with respect to a stationary weight. The potentiometer was specifically designed to have a knob attached to the shaft thereof on which could be exerted a large force to thereby rotate the shaft and adjust the resistance. Accordingly, the rotary motion of the shaft along with the weight when the housing was turned with respect thereof, was not found to be sufficiently smooth so as to result in the desired degree of accuracy thereof. Furthermore, the fact that the potentiometer was a separate entity installed into a housing as manufactured made the inventive goniometer extremely large and cumbersome and thereby unusable to any degree with small joints such as those between bones of a finger or a toe, for example. Thus, it was concluded that a new electronic goniometer would have to be developed which was compact and lightweight and usable to measure the range of motion between any two joints of the body regardless of size.

In another aspect, the prior art was found lacking when it came to providing a device enabling the close monitoring of the range of motion of various joints of the body during the performance of repetitious exercises. A physician would prescribe for a patient a series of sets and repetitions of a particular exercise, and although the patient would perform the exercises, the patient would not perform them through the prescribed range of motion and accordingly, such exercises would prove to be useless in the rehabilitation of the patient. Thus, a device was needed which could measure sets and repetitions of exercises performed on various joints of the body while requiring that the joints be exercised through the prescribed minimum range of motion.

SUMMARY OF THE INVENTION

Thus, in order to overcome the above described deficiencies and shortcomings found in the prior including the prior art as embodied in the invention disclosed in the patent application, the present invention was devised as a means of advancing the state of the art significant steps forward from the state of the art as embodied in the invention disclosed in the parent application. Thus, the present invention includes the following features;

(a) The present invention includes a newly designed electronic goniometer which overcomes all of the deficiencies found in the prior art designs. The electronic goniometer is of the resistance type and includes a small lightweight preferably plastic casing having an inner chamber of a substantially circular periphery. On the periphery of this chamber is mounted an extremely thin resistor film formed in an elongated strip and extending over most of the circumference of the chamber. The resistor film, in the preferred embodiment, is made of a highly mechanically oriented carbon material with unidirectional crystals therein. Rotatably mounted within the chamber is a pendulum device having an extremely small wiper contact at the bottom thereof. Two contact wires are provided for the electronic goniometer one of which attaches to the resistor film and the other of which is electrically connected to the wiper contact. Thus, as the housing moves with respect to the pendulum which maintains a vertical orientation with respect to the center of the earth, the wiper contact moves along the resistor film thereby defining a resistance which varies with the movement of the housing with respect to the pendulum. This resistance may be converted to a voltage which is inputted into the micro-computer contained in the modular housing of the present invention. The pendulum bearings are of sufficient quality so as to enable the pendulum to freely swing even if the housing is tilted up to 70° in a direction perpendicular to the direction of rotation of the pendulum.

(2) The modular housing of the present invention includes a mode switch enabling the choosing of a range of motion mode or a bio-feedback mode. The modular housing further includes a display, a tape printer, a set of buttons enabling the choosing of a direction of motion, a set of buttons enabling the choosing of the type of examination and a set of buttons enabling the inputting of numerical entries such as those relating to sets and repetitions of exercises to be performed when the mode switch is in the bio-feedback position. A reset switch is also provided to enable the device to be reset after each measurement sequence has taken place. Further, a digital display is provided so as to enable displaying of the various measured ranges of motion thereon.

Within the modular housing is housed a micro-computer which is the heart of the present invention and which has connected thereto electronic circuitry enabling the micro-computer to receive signals from the above described electronic goniometer which signals may be converted into angles which may be displayed, retained in a computer memory and/or printed out by the printing unit. The modular housing further includes a software input which enables different computer programs to be interfaced with the micro-computer to thereby add flexibility to the invention. Further, the modular housing includes a plurality of cord connections which enable a plurality of electronic goniometers to be simltaneously connected thereto so that special measurements such as those relating to the range of motion of one vertebral joint with respect to another vertebral joint may be undertaken.

(4) The present invention may be utilized in one of two modes, a first mode wherein particular ranges of motion of particular body joints may be accurately measured and a second mode wherein a partciular joint may be exercised through a predetermined sequence of repetitions and sets with each repetition being made through a predetermined range of motion. In this mode, the micro-computer monitors the range of motion through which the joint travels during the exercises and only indicates that a repetition has been completed when the prescribed range of motion has been attained.

(5) In a further aspect of the present invention, the modular housing may include an input connection enabling the connection thereto of a remote control enabling the freezing of a range of motion reading for retention, display and/or printing. In a further aspect, the inventive electronic goniometer may include in its casing hardware enabling the display thereon of the particular measured range of motion, enabling resetting of the goniometer and enabling the freezing of a reading, as well as enabling control of the activation thereof.

(6) the above described software may include aspects thereof which program the invention so that different printouts for the printing mechanism may be obtained. For example, printouts may be obtained through the software programming of active ranges of motion, degrees of flexion, repetitions and sets of particular exercises which exercises are also printed for reference, etc. The present invention as embodied in the modular housing, the one or more goniometers, the software which may be inputted thereto and the remote control freeze button may be completely self contained within a suitcaselike container which enables the invention to be easily packed up and transported to its point of use.

Accordingly, it is a first object of the present invention to provide a device enabling the measurement of the range of motion of various joints of the human body to within an accuracy of ±1°-2°.

It is a further object of the present invention to provide a device enabling the recording of sets and repetitions of exercises performed by the various joints of the body during the rehabilitation thereof.

It is a further object of the present invention to provide a device wherein any measurements, sets and repetitions measured thereby may be displayed, stored and/or printed out on paper mounted therein, preferably in roll form.

It is a yet further object of the present invention to provide such a device including a lightweight compact electronic goniometer which is sufficiently small and lightweight so as to enable its attachment to any joint of the human body for measurement of the range of motion thereof.

It is a yet further object of the present invention to provide such an electronic goniometer which may, if desired, include a display thereon as well as controls therefor.

It is a still further object of the present invention to provide a device which may be programmed as desired through the selective attachment thereto of diverse preprogrammed cassettes, each of which programs the micro-computer thereof to perform unique predetermined functions.

It is a still further object of the present invention to provide a device wherein a plurality of electronic goniometers may be attached thereto so as to simultaneously measure relative ranges of motion of different body joints simultaneously, such as different adjacent joints of the spinal column.

It is a still further object of the present invention to provide a device which may be easily packed up and transported to its point of use in a convenient packaging scheme.

These and other objects, aspects and features of the present invention will be better understood from the following description of the preferred embodiments when read in conjunction with the appended drawing figures.

SPECIFIC DESCRIPTION OF THE PREFERRED EMBODIMENTS

Figure 1:
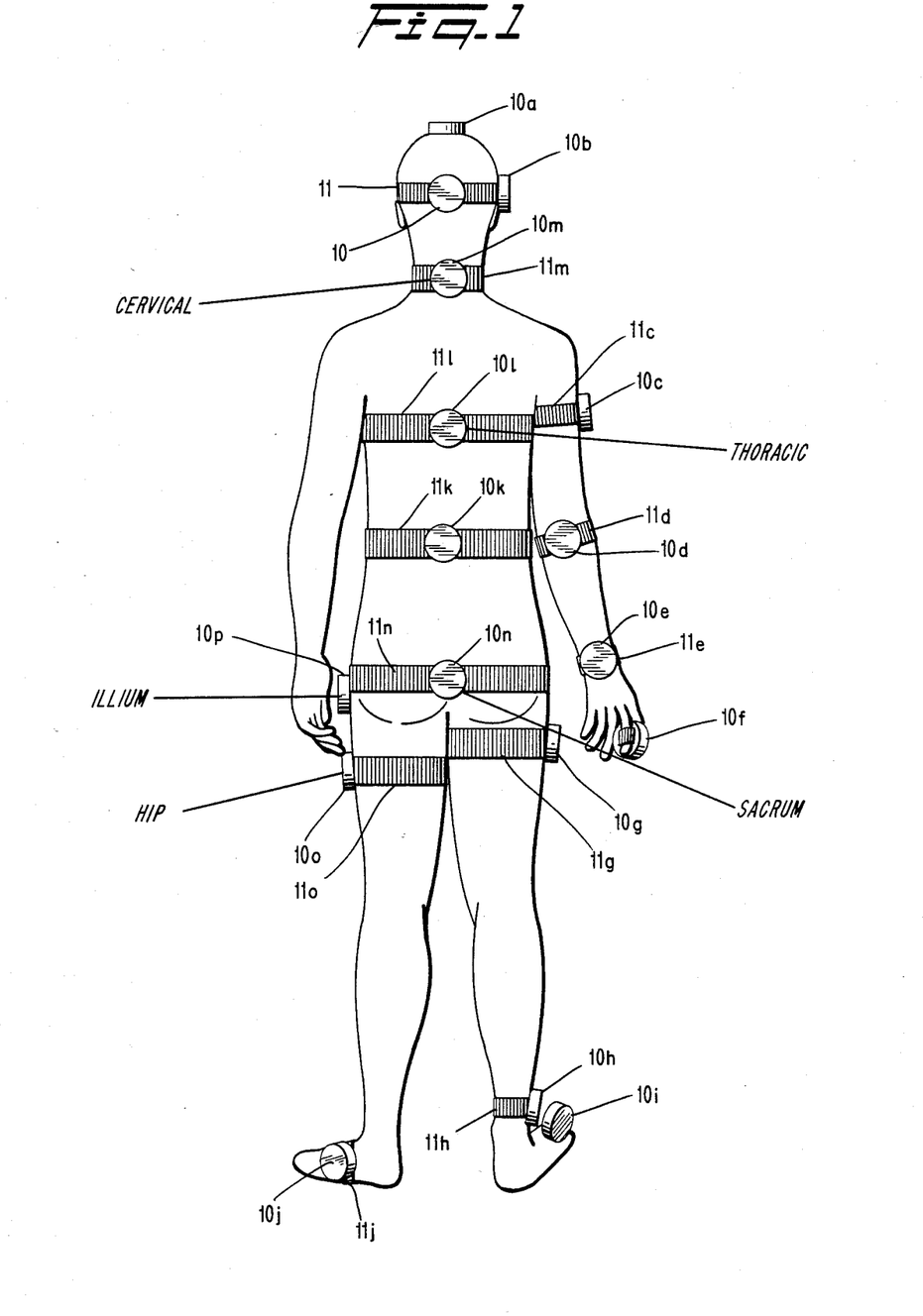
FIG. 1 shows a schematic representation of the human body with goniometers in accordance with the present invention attached to various ones of the joints thereof for range of motion measurements.

As shown in FIG. 1 of the drawings, the present invention includes an electronic goniometer 10 which may selectively be attached at various locations on the human body so as to enable measurements of the range of motion of the various joints thereof. As shown in FIG. 1, the electronic goniometer 10 is attached to the skull by virtue of an elastic band 11. Further, electronic goniometers 10a, 10b, 10c, 10d, 10e, 10f, 10g, 10h, 10i, 10j, 10k, 10l, 10m, 10n, 10o and 10p are also shown connected to various portions of the body in some cases by corresponding elastic members 11.

Figure 5:
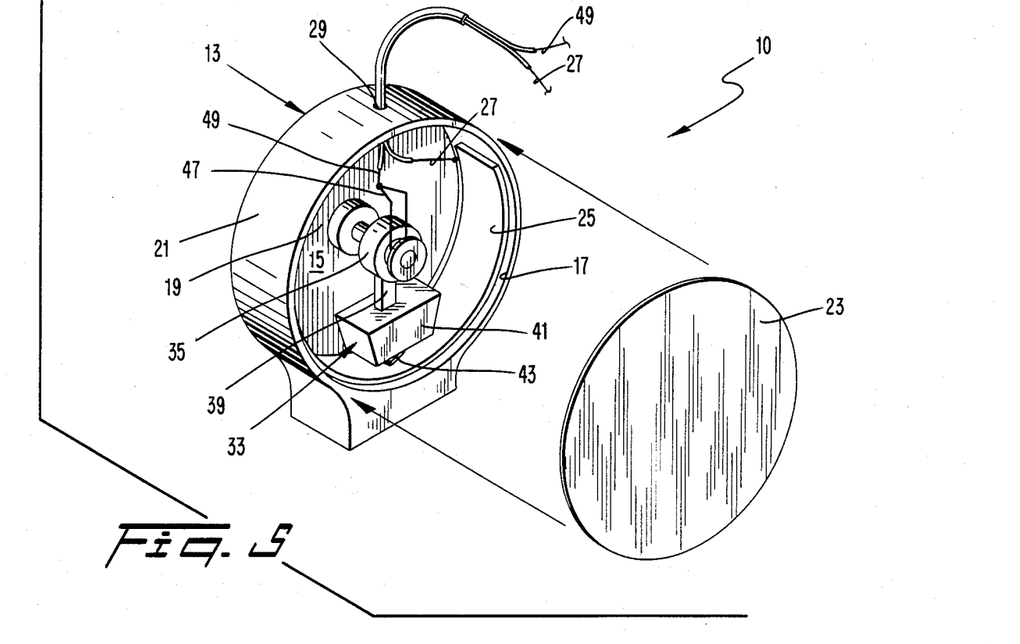
FIG. 5 shows a perspective view of one embodiment of the goniometer of the present invention with the cover removed to show detail.
Figure 6:
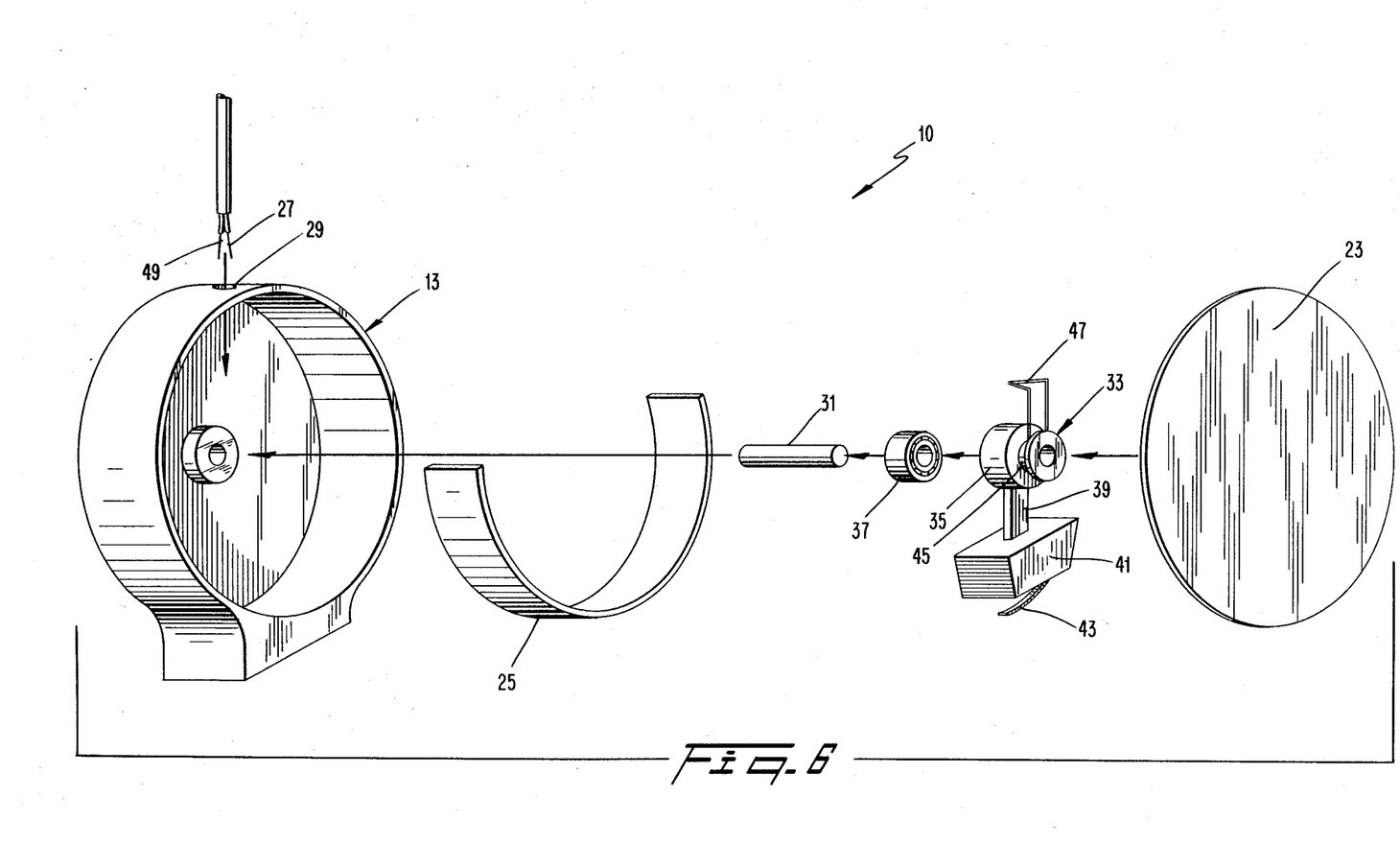
FIG. 6 shows an exploded view of the electronic goniometer depicted in FIG. 5.
Figure 7:
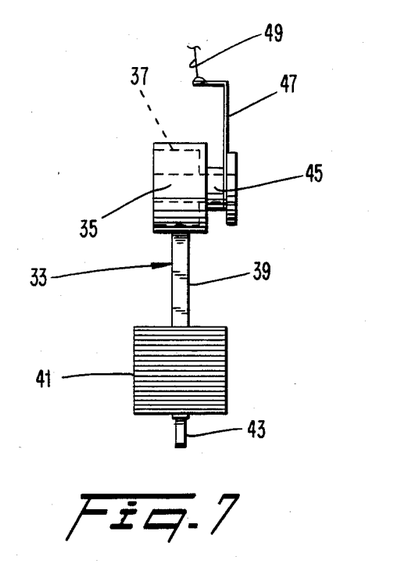
FIG. 7 shows a side view of the pendulum and wiper contact of the inventive electronic goniometer.

With reference now to FIGS. 5-7, it is seen that the inventive electronic goniometer 10 includes an outer casing 13 having an inner chamber 15 defined by substantially circular peripheral walls 17. The casing 13 includes a back wall 19 connected to a peripheral wall 21 which defines the substantially circular outer periphery of the inner chamber and a cover 23 which is removeably attached to the sidewall 21.

As best seen with reference to FIGS. 5 and 6, the wall 17 of the chamber 15 has mounted thereon a resistor film 25 which is made of an extremely thin film of highly mechanically oriented carbon with uni-directional crystals therein, which resistor film 25 is extremely sensitive to electrical current. The resistor film 25 extends over the major portion of the circumferences of the walls 17, preferably over 256° of the circumference at least, so as to give the electronic goniometer 10 increased flexibility in orientation. Connected at one end to the resistor film 25 is a contact wire 27 which is extended through an opening 29 formed in the wall 21 of the casing 13.

The back wall 19 of the casing 13 has rigidly mounted thereon a shaft 31 which extends virtually across the entirety of the width of the wall 17. If desired, the shaft 31 may be sufficiently long so that it enters an opening (not shown) in the cover 23 for purposes of stability. In view of the lightweight nature of the component parts of the electronic goniometer 10, such additional shaft mounting structure is not necessary. At the end of the shaft 31, a pendulum 33 is mounted which includes a collar portion 35 having a bearing 37 therein which allows the collar 35 to be mounted over the shaft 31 while allowing easy rotation of the pendulum 33 with respect thereto. The bearing 37 is of sufficient quality so as to enable the pendulum 33 to freely swing even if the casing 13 is tilted up to 70° in a direction perpendicular to the direction of rotation of the pendulum 33.

If desired, the bearing 37 may comprise a ball baring or if desired, may comprise any kind of bearing so long as frictional forces between the bearing 37 and the shaft 31 are kept at an absolute minimum.

The pendulum 33 further includes a neck portion 39 which connects the collar 35 to a weight 41. On the underside of the weight 41, a wiper contact 43 is provided which is made of a flexible wire-like member which is designed to resiliently engage the resistor film 25 as the housing 13 moves with respect to the pendulum 33 which maintains a position with respect to the center of the Earth as close to vertical as is possible depending upon the particular orientation of the casing 13, due to the force of the Earth's gravity.

As best seen with reference to FIG. 7, the collar 35 includes a recessed area 45 into which is mounted a wiper contact 47 which is connected to a wire 49 extending out of the casing 13 through the hole 29. The pendulum 33 is made of an electrically conductive material so that when the device is assembled as shown in FIG. 5, an electrical connection is made between the wire 27, the resistor film 25, the wiper contact 43, the pendulum 33, the wiper contact 47, and the wire 49. Thus, as the position of the casing 13 varies with respect to the vertical position of the pendulum 33, the resistance as defined between the position of the wiper contact 43 on the resistor film 25 and the wire 27 correspondingly varies. Thus, as this resistance varies, in a correspondingly manner, the voltage across the wires 27 and 49 with a steady source of electrical power connected thereacross also varies in a predictable and measureable manner.

Figure 2:
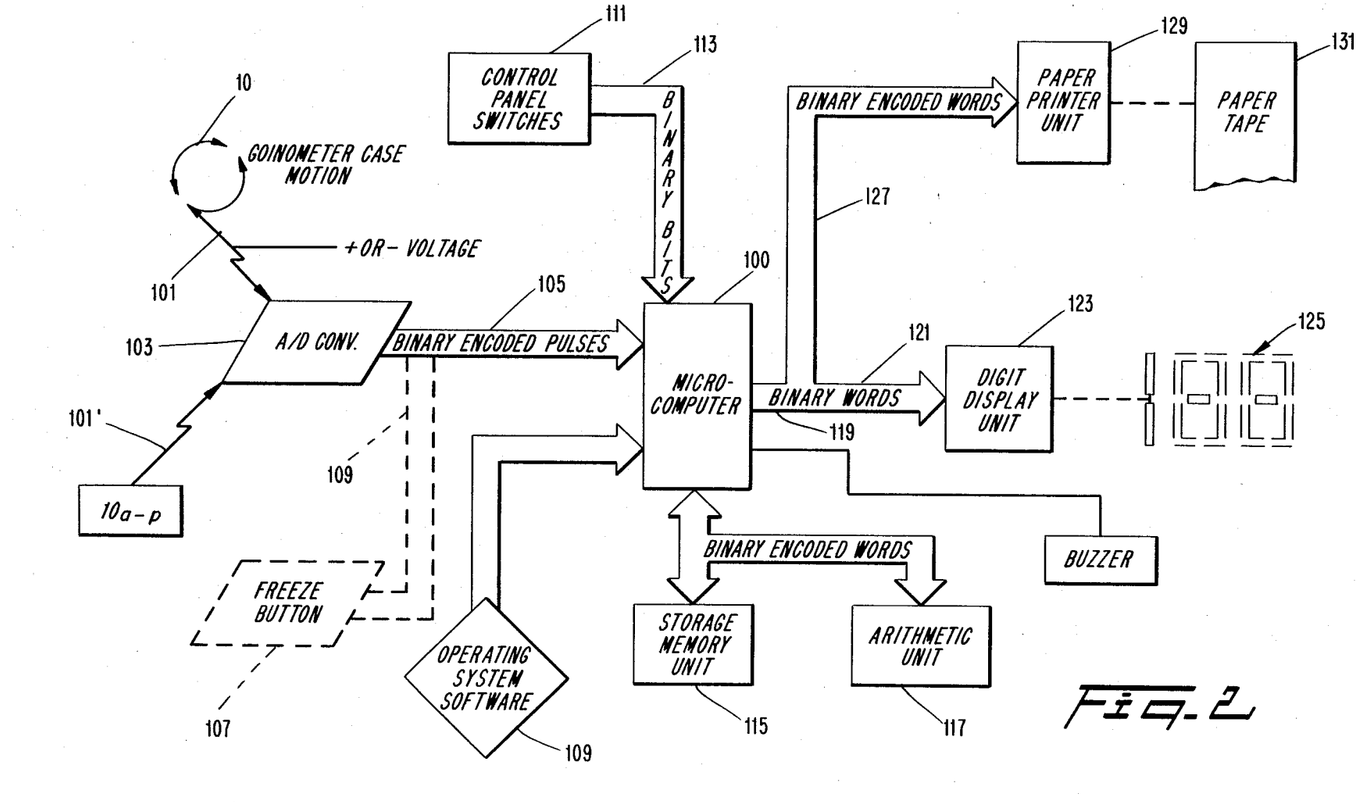
FIG. 2 shows a block diagram of inputs and outputs in a representative micro-computer for the present invention.
Figure 3:
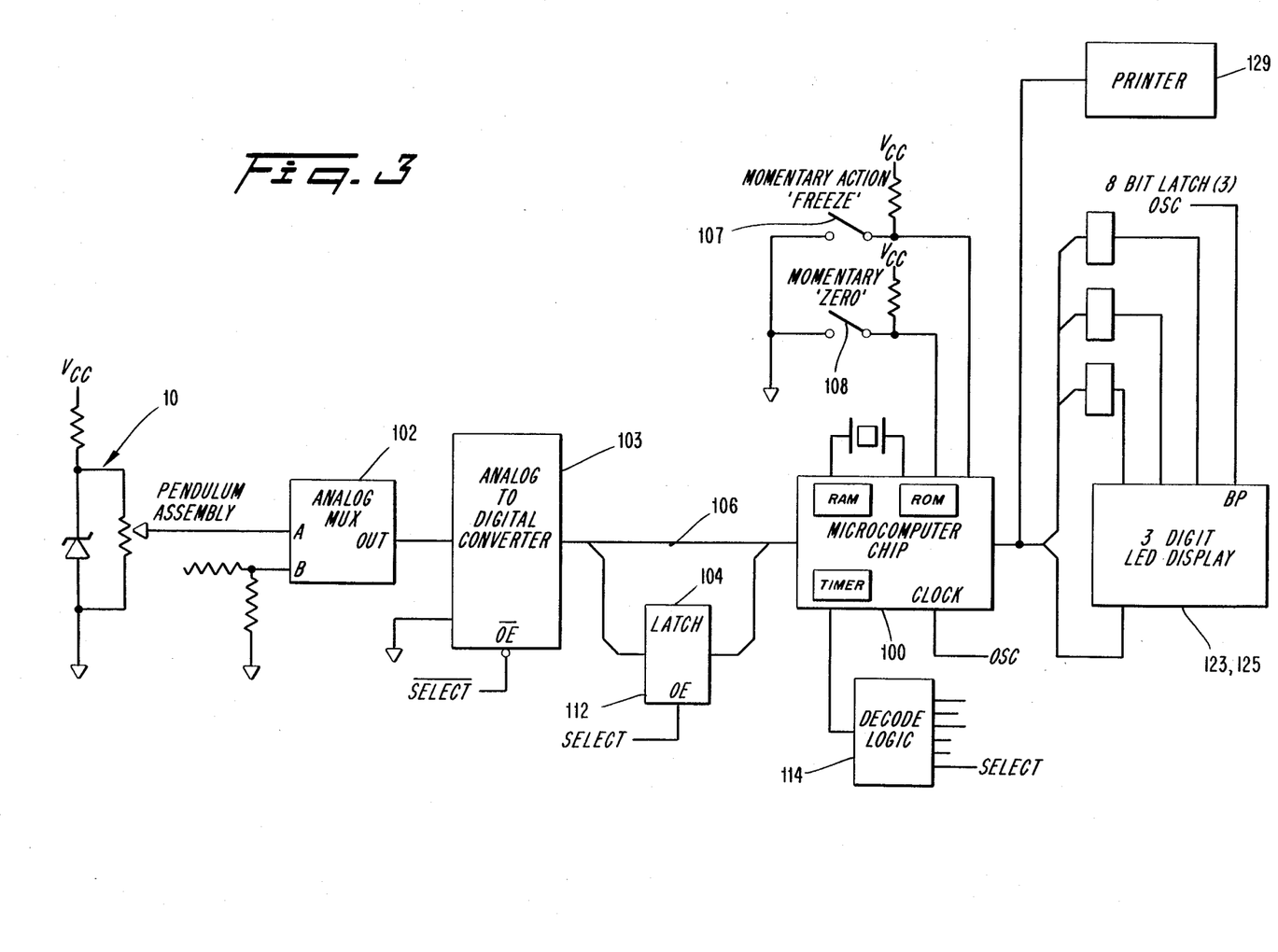
FIG. 3 shows a schematic electrical circuit depicting the micro-computer and associated connections.
Figure 4A:
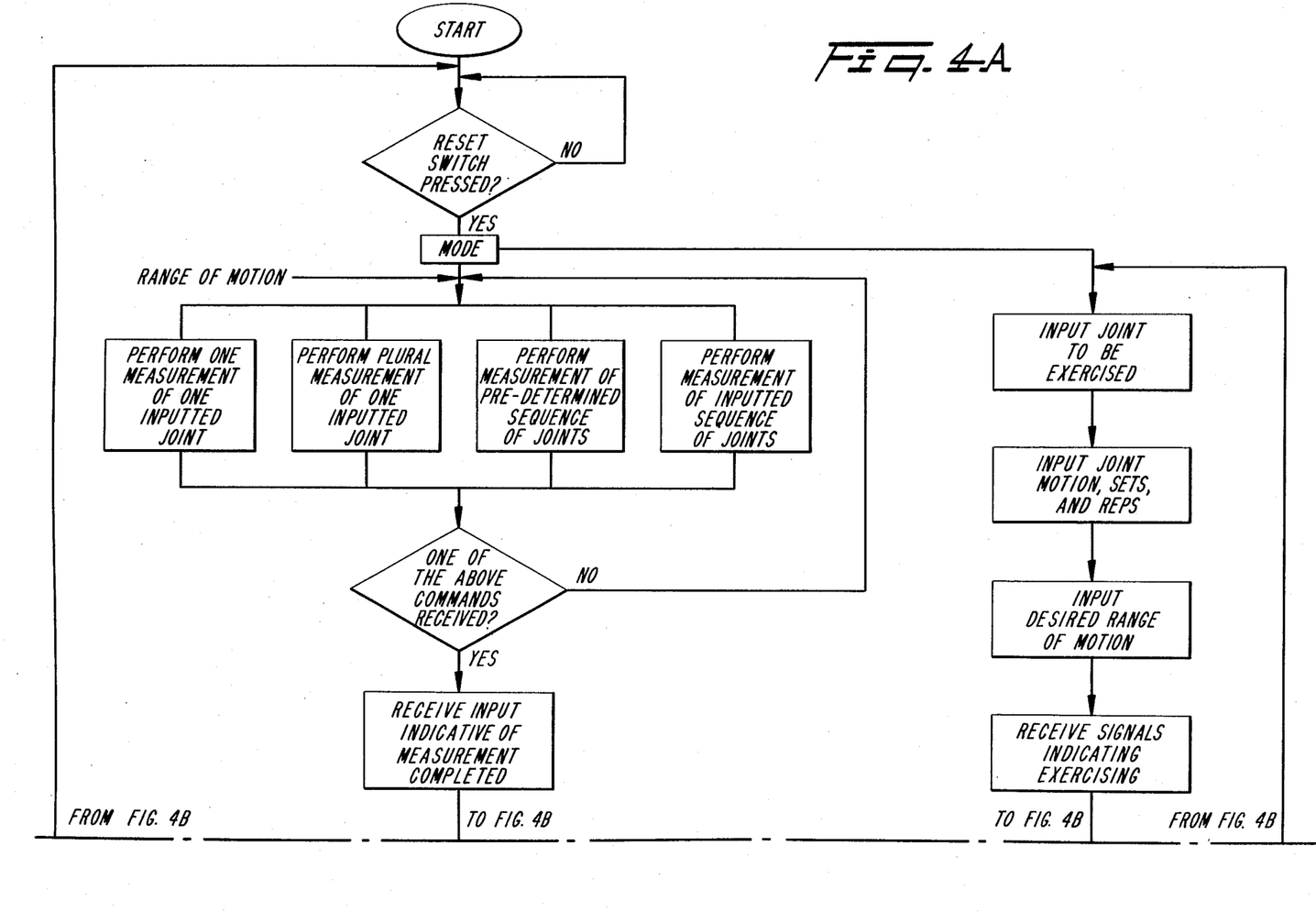
FIG. 4a and b show a flow chart of the operation of the present invention.
Figure 4B:
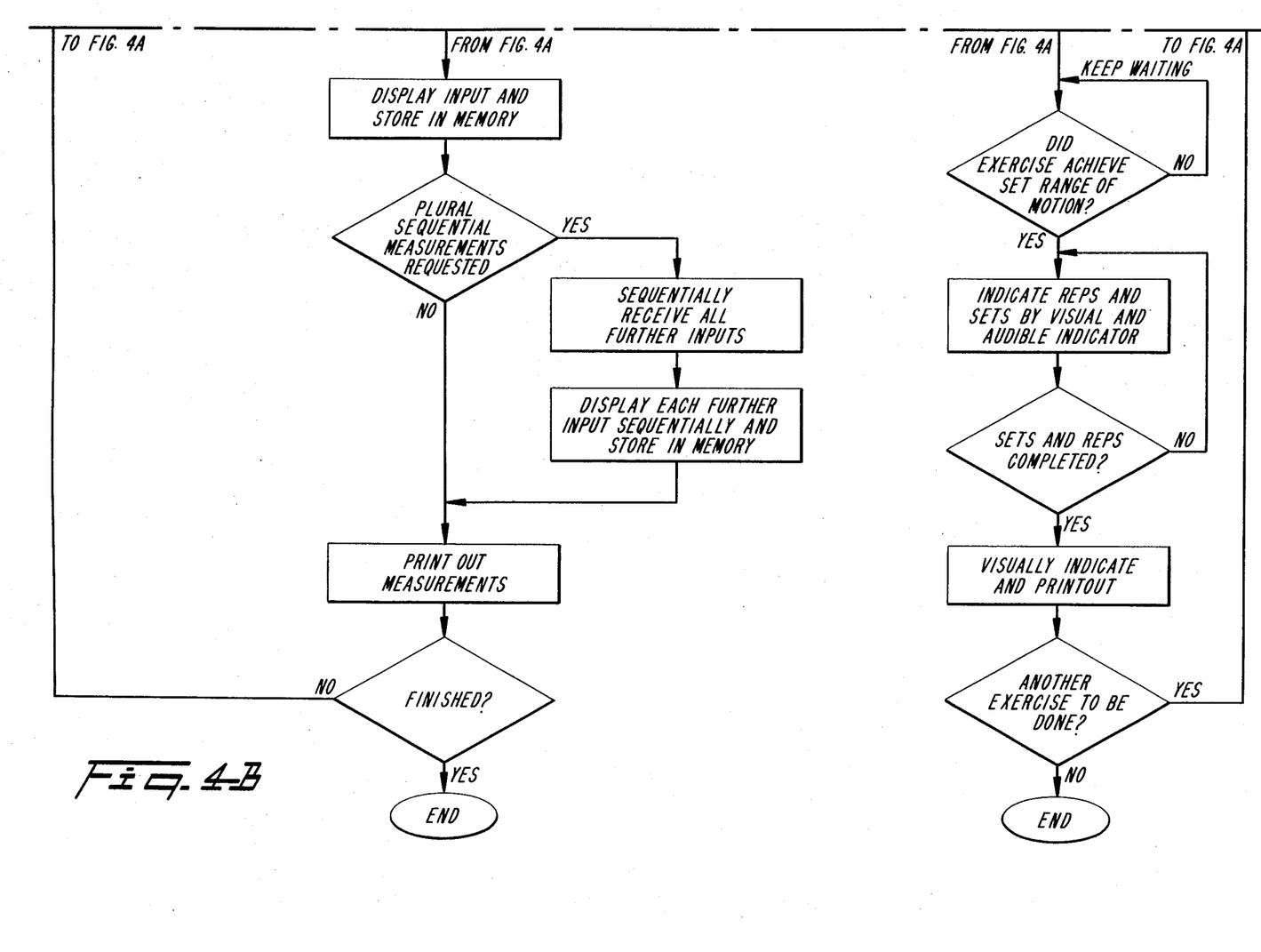

Reference is now made specifically to FIGS. 2–4, wherein a general and specific explanation of the internal electronics of the present invention will be made. Firstly, reference is made to FIG. 2 which shows a block diagram of the inputs and outputs for the micro-computer of the present invention. As shown in FIG. 2 schematically, a micro-computer 100 comprises the heart of the system. The electronic goniometer 10 is seen to emit a voltage output 101 which output is received by an analog-to-digital converter 103 which converts the analog voltage signals 101 into a digital form compatible with the circuitry of the micro-computer 100. The line 105 carries theses binary encoded pulses to the micro-computer 100. Additionally, a box labeled 10a–p is seen to be connected to the analog-to-digital converter 103 via a voltage line 101, 101′. The box labeled 10a–p is provided so as to represent a plurality of additional electronic goniometers 10a–p as depicted in FIG. 1 of the drawings, which additional electronic goniometers may as desired be connected into the system. Additionally, a box labeled 107 is shown to connect to the line 105 via a further line 109. The box 107 is shown to represent a freeze button which may be selectively actuated to freeze the reading of the goniometer 10 or 10a–k at whatever reading exists at the moment at which the freeze button is depressed. The line 109 is tapped into the line 105 so as to represent the fact that the freeze button stops further transmissions from the analog-to-digital converter to the micro-computer upon the actuation thereof so as to freeze whatever reading has been received by the micro-computer at that moment.

With further reference to FIG. 2, it is seen that operating system software designated by the reference numeral 109 may be selectively plugged into the micro-computer 100 so that various unique programs may be utilized to control the micro-computer in predetermined ways. Further, the control panel switches are designated by reference numeral 111 which control panel switches communicate in binary form with the micro-computer 100 via the line 113.

Again, the reference numeral 100 refers to the microcomputer which forms the heart of the system shown in FIG. 2. The micro-computer 100 comprises a micro-processor circuit that operates under the control of the software 109 so as to interpret the binary encoded angles sent thereto in the line 105 and to store the true angles in the memory unit designated by reference numeral 115. The storage memory unit is used by the micro-computer 100 to store the current angular reading as received by the line 105 and also to store whatever sequence of measurements is to be made as inputted by the control panel switches 111 and so as to further identify whichever switches on the control panel have been depressed during the present operational cycle. Also shown in FIG. 2 is an arithmetic unit 117 which is utilized by the micro-computer 100 to calculate the number of degrees of movement of the electronic goniometer 10 with respect to an established reference point. The established reference point is determined immediately before the angle is measured by depressing a "zero" key on the control panel 111 as will be described in greater detail hereinafter.

As further shown in FIG. 2, an output line 119 is provided from the micro-computer 100 with a first branch 121 thereof leading to a digital display unit 123 which, in the preferred embodiment, comprises a series of light emitting diodes, designated by reference numeral 125. A second branch 127 of the line 119 leads to a paper printer unit 129 which may print a permanent record of the examination results as represented by reference numeral 131 and as described in greater detail hereinafter. The actuation of the paper printer unit 129 may be selectively accomplished by depression of the appropriate buttons on the control panel 111 or may be auotmatically accomplsihed at some point during an examination sequence.

Reference is now made to FIG. 3 which shows the details of the system depicted in FIG. 2 in the form of an electrical circuit. FIG. 3 shows a single electronic goniometer 10 connected to the analog-to-digital converter 103 via an analog multiplexer 102. The analog multiplexer 102 is provided with one input port A for the goniometer 10 and a further input port B for an additional electronic goniometer as explained hereinabove. Of course, if desired, the analog multiplexer 102 may have as many input ports as necessary to connect however many electronic goniometers are required depending upon the measurements which are to be conducted. The analog-to-digital converter 103 is connected to the micro-computer 100 via a line 106 having bridged thereon a latch device 112 which is provided to take the asynchronous output of the analog-to-digital converter 103 and capture it and retain it therein for later reading by the micro-computer 100.

As further shown in FIG. 3, a decode logic device 114 is provided which arbitrates between the various devices which are connected to the micro-computer as to which device will talk to the micro-computer 100 at any given instant. Thus, the decode logic device 114 prevents bus contention. FIG. 3 also shows in electrical schematic form the freeze button designated by reference numeral 107 and also shows the zero button designated by reference numeral 108 which was briefly described ablove. The zero button 108 is provided so that in virtually any orientation of the electronic goniometer 10, if the zero button 108 is depressed, the electronic goniometer 10 will be considered to be reading zero degrees in that orientation so that further movement by the electronic goniometer 10 will result in range of motion readings which are taken with respect to the precise position of the electronic goniometer when the zero button 108 was depressed.

FIG. 3 further shows the printer 129 and the LED display device 123, 125. Other aspects of the circuitry which are shown in FIG. 2 such as for example the storage memory unit 115, the arithmetic unit 117, the operating system software 109 and the control panel switches 111 are not shown in FIG. 3 for reasons of clarity.

Figure 11:
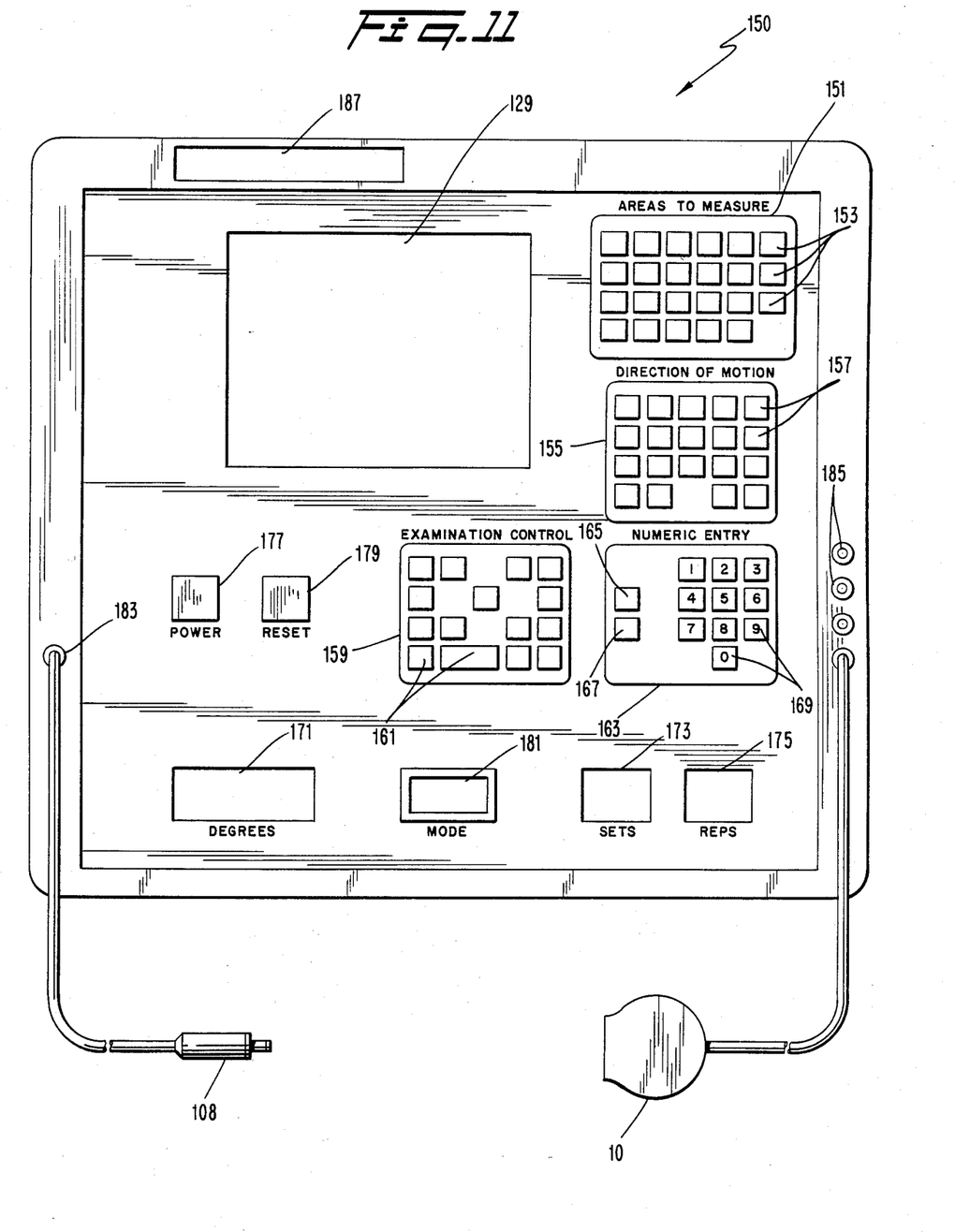
FIG. 11 shows a schematic depiction of the modular housing of the present invention.

Reference is now made to FIG. 11 wherein an example of one configuration of the modular housing described hereinabove is shown. The modular housing 150 is generally seen to include a large number of buttons and switches which were previously designated by the general reference numeral 111. As seen in FIG. 11, these buttons are divided up into several separate related areas of function. Thus, a first block of buttons 151 includes a series of buttons 153 each of which when depressed indicates to the micro-computer 110 that a specific joint of the body is to be measured. Examples of these joints are: interphalangeal, metcarpophalangeal, metatarsophalangeal, carpometacarpal, distal interphalangeal, proximal interphalangeal, thumb, index, finger, mid-finger, ring finger, little finger, wrist, elbow, shoulder, great toe, second, third, fourth and fifth toe, ankle, knee, hip, cervical, dorso lumbar. A further block of buttons 155 includes further buttons 157 each of which when depressed indicates to the micro-computer 100 that a particular direction of motion is to be undertaken in the joint chosen in the block of buttons 151. Examples of directions of motion which may be indicated through depression of one of the buttons 157 are as follows: inversion, eversion, flex, extension, abduction, adduction, supination, pronation, rotation, lateral bend left and right, dorsi flex, palmer flex, radial div, ulnar div, plantar flex, etc.

As further shown in FIG. 11, a further block of buttons 159 is provided which includes therein a plurality of buttons 161. The block of buttons 159 includes buttons which relate to examination control. Thus, when one or more of the buttons 161 are depressed, the following pieces of information are fed to the micro-computer 100 as to a type of examination which is contemplated: (1) ankylosis, a condition of a joint in which the movements are restricted by malfunction, malformation or union of bones; (2) active motion, the motion of a joint without assistance from an outside party; (3) passive motion, motion of a joint with the assistance of an outside force such as a therapist or machine, etc.; (4) amputate, the absence of body part that normally would have a range of motion; (5) lag, indicating that there is a negative lag due to disability; (6) left, indicating that examination is being undertaken with the particular joint indicated on one of the buttons 153 located on the left side of the body; (7) right, indicating that the joint indicated on one of the buttons 153 is that which is located on the right side of the body. Additionally, other buttons 161 may be provided in the block of buttons 159 to indicate to the micro-computer 100 an event goal which is utilized as will be explained in greater detail hereinafter when the present invention is used in a biofeedback mode. Further, a print button may be provided in this block of buttons 159 to instruct the computer to print the result of the current examination in whatever mode the invention has been operating under. A further button may be provided to instruct the device to print a duplicate copy of the printed results. Further, a paper feed button may be provided so that when the roll of paper in the printer 129 is empty, a new roll may be installed and the paper thereof may be moved so as to install the paper roll properly. The block of buttons 159 may further include the zero button and freeze button explained more particularly in FIG. 3 with the respective reference numerals 108 and 107. Additionally, a button may be provided in the block of buttons 159 which when depressed clears the internal memory 115 (FIG. 2) of all entries made since the last depression of a print button.

Further, the block of buttons 159 may include a button designated with the word "enter" which may be utilized in conjunction with the above described button for "event goal" which enter button will be utilized as explained in greater detail hereinafter. Further, the block of buttons 159 may include an end of exam button which when depressed causes the printer 129 to print the patient's name, the date and a further code if desired on the roll of paper.

As further seen in FIG. 12, the housing 150 further includes a block of buttons 163 having numerical buttons labeled 0-9 and two further buttons designated by the reference numerals 165 and 167. The button 165 when pressed indicates the microcomputer 100 that the operator thereof is going to input a number utilizing the buttons 169 indicative of the number of sets of a particular exercise previously entered through the buttons 153, 157 and 161 which are to be performed. The button 167 when depressed indicates to the micro-computer that the operator thereof is going to enter a number in the numerical buttons 169 indicative of the number of repetitions of the above described exercise which are to be performed in each set. The operation of the buttons in the block of buttons 163 in conjunction with the buttons in the block of buttons 159 concerning "event goal" will be described in greater detail hereinafter.

With further reference to FIG. 11, it is seen that a display 171 has been provided to display the degrees of movement of a joint during the operation of the device. Also, a display 173 is provided to display the number of sets which have been entered through the use of buttons 165 and 169 and a further display 175 has been provided to display the number of repetitions which have been entered through the use of the buttons 167 and 169. The displays 171, 173 and 175 when taken together comprise the display designated in FIGS. 2 and 3 by reference numeral 125.

Further, as shown in FIG. 12, the device 150 includes a button 177 which is operative to turn the device on and off, a reset button 179 which erases all previous data and places the device 150 in condition for a further entry of information and for the further performance of an examination. Further, the device 150 includes a mode button 181 which enables the device to be switched between the two possible modes of operation, a first mode wherein the invention is utilized to determine the range of motion of the joints of the body and a second mode called the "biofeedback" mode wherein exercises may be performed on particular joints through prescribed ranges of motion in prescribed sets and repetitions as will be described in greater detail hereinafter. Further, the device 150 includes an input socket 183 shown having connected thereto the freeze button 108 and includes further input sockets 185 which enable the connection to the device 150 of one or more goniometers 10.

As further shown with reference to FIG. 11, an opening 187 is provided in the device 150 for the purpose of selective insertion of preprogrammed software tapes which enable the invention to be operated in a prescribed manner.

The present invention is specifically designed with sufficient variety of button controls so that it may achieve any desired flexibility based upon reason of economy or diversity of examinations required. The present invention is designed so that different software packages may be purchased in conjunction therewith so as to enable different levels of sophistication of measurement and biofeedback to be attained. For example, one orthopedic surgeon might merely specialize in the spinal column, whereas another orthopedic surgeon might merely specialize in problems with the joints of the legs and hips. Thus, the surgeons specializing the spinal column could purchase a software package which when inserted into the slot 187 shown in FIG. 12 would enable the computer 100 to receive inputs from those buttons 153, 157 and 161 relating to measurement of ranges of motion of the various joints of the spinal column. As a further example, the above described surgeon specializing in the joints of the legs and hips could purchase a software package which when inserted into the slot 187 would enable the micro-computer 100 to receive inputs from those buttons 153, 157 and 161 relating to the joints of the legs and hips. Further, either of the software packages described above would enable the micro-computer to control the invention so as to program therein exercises of sets and repetitions with particular joints through the use of the buttons 161, 165, 167 and 169 when the mode button 181 is moved to the biofeedback position.

At present, three particular software programs have been devised by Applicant and will be described in detail hereinafter, but it is to be stressed that these software programs are merely examples of the infinite number of programs which could be devised so as to be operable in conjunction with the present invention. A first program has been specifically designed for research people and also for physicians who have the opportunity to spent a lot of time with each patient. This program is designed so that every single button which has been described hereinabove may be utilized in the examination of a patient. The program requires the physician to push the appropriate buttons in each block of buttons 151, 155, 159 and 163 so as to proceed with the examination and further requires the physician to press the appropriate buttons to allow the device to print out the results.

A second program which has been devised by applicants enables the present invention to operate in a "grouping of points" mode. In this mode, the physician or examiner can pick groups of movements for a particular joint which may be sequentially measured through the mere depression of a button in the block of buttons 159. For example, in order to completely examine the range of motion of a shoulder, six separate measurements must be obtained as to extension, flexion, abduction, adduction, external rotation and internal rotation. Thus, with this program in place, the physician or examiner can input on the block of buttons 151 that the shoulder is to be measured and may input a single button in the block of buttons 159 to indicate that the sequence of ranges of motion is to be obtained. Then, the electronic goniometer is appropriately attached to the shoulder and sequential depression of one of the buttons 108, 161 will result in a later print out of sequential measurements of the various ranges of motion as set forth hereinabove. In this program, a plurality of the electronic goniometers may be attached to the device by virtue of the input sockets 185 so as to allow the simultaneous measurement of two or more joints which may move together simultaneously, such as for example the elbow and the shoulder.

A third program has been devised by Applicants which allows measurements of the lumbar and cervical spine regions. Thus, with the appropriate plurality of electronic goniometers attached at the input sockets 185, the patient, e.g. may flex and touch the floor while the device measures the range of motion of the joints to which the electronic goniometers are attached so as to be able to determine the particular range of motion of each individual joint. In this regard, the numerical buttons 169 may be utilized so as to pinpoint for the computer the exact joint which is being measured. For example, the physician or examiner may depress the appropriate buttons 153 indicating that one of the thoracic joints is being examined and may depress the numerical buttons 169 to indicate which particular thoracic joint is being examined, such as for example "thoracic 12." Then, after depressing the appropriate direction of motion buttons 157, and examination control buttons 161, the examination may be undertaken. In a further aspect, the two electronic goniometers may be placed at the locations depicted in FIG. 1 by reference numerals 10*l* and 10*n*. If desired, the entire back may be examined through the simultaneous use of electronic goniometers 10*m*, 10*l'*, *10k*, 10*n*, 10*o* and 10*p*.

Figure 8:
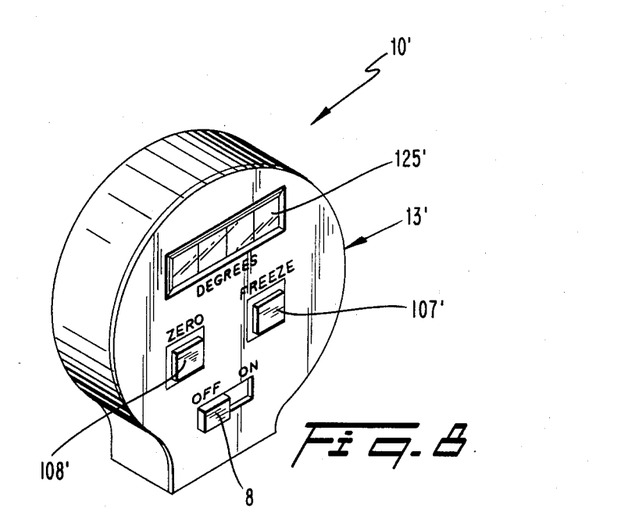
FIG. 8 shows a perspective view of a further embodiment of the electronic goniometer of the present invention.
Figure 9:
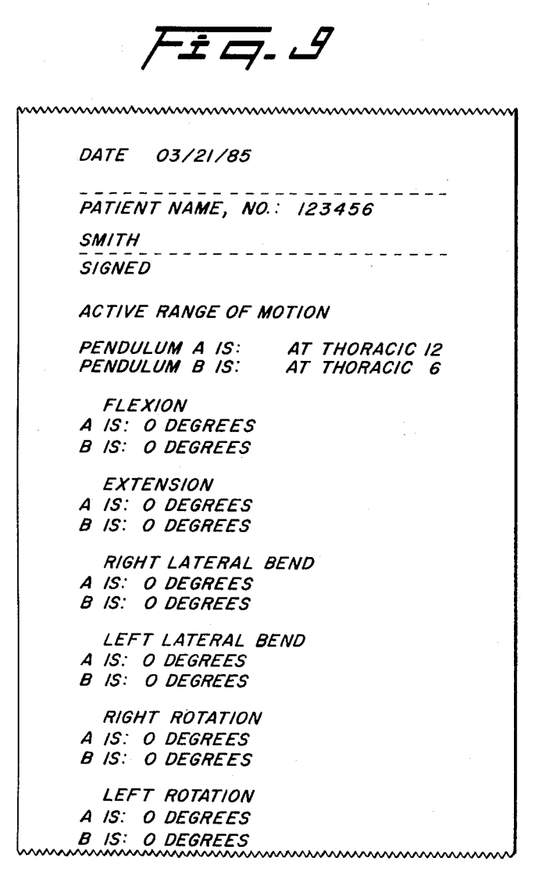
FIGS. 9 and 10 show representative print outs which may be obtained from the present invention in different modes of operation thereof.

Reference is now made to FIG. 8 which shows the details of the outer casing 13' of an electronic goniometer 10'. As shown in FIG. 9, the electronic gonimeter 10' may be provided with an on-off switch 8, a zero button 108', a freeze button 107' and a display 125'. In order to render this electronic goniometer 10' compatible with the device designated by reference numeral 150, the electronic goniometer sockets 185 may be provided with extra receptacles therein so as to receive extra pins on the electronic goniometer plug so that the functions attributable to the devices 107', 108', 125' and 8 may be interfaced with the system. For example, when the electronic goniometer 10' is used, the plugging in of the electronic goniometer 10' into its appropriate socket 185, may, if desired, result in the de-activation of the freeze and zero buttons on the control panel 111 thereof when the switch 8 is at the on position. Regardless of the position of the switch 8, with the electronic goniometer 10' connected to the device 150, both the displays 125 and 125' will be operable. The electronic goniometer 10' will include therein all of the structure shown and described hereinabove with reference to FIGS. 5–7 in addition to those aspects particularly shown in FIG. 8.

Figure 10:
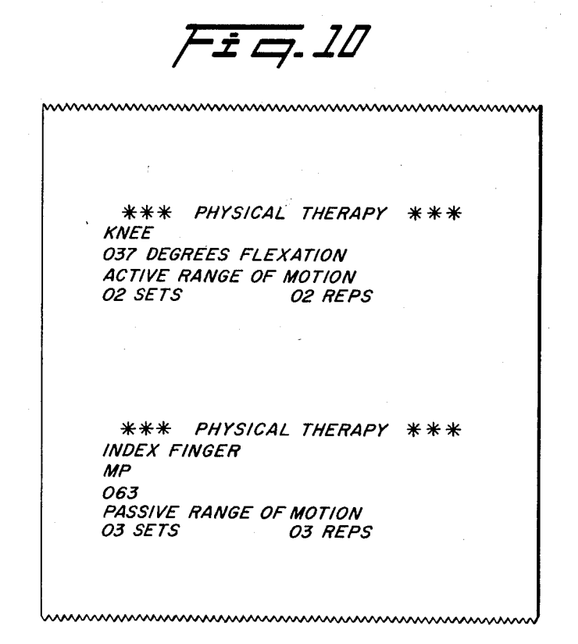

FIG. 9 shows a typical print out made through the use of two electronic goniometers A and B measuring the range of motion of the thoracic 12 joint and thoracic 6 joint during movements thereof as set forth therein. FIG. 10 shows a typical print out of exercises performed with the switch 181 switched to the biofeedback mode which print out indicates the particular joint, the required range of motion, the type of range of motion, and the sets and repetitions completed. These print outs are merely examples of the infinite number of types of print outs which may be accomplished by the printer 129 through the infinite uses of the present invention as set forth hereinabove.

Reference is now made to FIG. 4 wherein a flow chart is set forth indicating typical modes of operation of the present invention. As set forth hereinabove, the present invention is specifically designed to not only enable the physician or examiner to check the range of motion of every joint of the body in every possible movement thereof, but is also, quite importantly, devised so as to enable a physicial or occupational therapist to use the device in the rehabilitation of a patient. Thus, after determination of the loss of range of motion of a particular joint through examination in the range of motion mode, the physical or occupational therapist may use the present invention so as to set up an exercise program specifically designed so as to enable the patient to slowly rehabilitate the joint in question until such time as the optimal range of motion has been attained. Thus, for example, let us assume that a particular joint has an optimal range of motion in a particular motion thereof, of 90° and that due to accident, injury or disease, that particular range of motion has been reduced to 70° as measured in the range of motion mode of the present invention. In such a situation, optimally, it would be desirable to rehabilitate that joint so that that particular range of motion would regain the 90° level. Thus, the physical or occupational therapist might prescribe a set of exercises to be performed with one or more electronic goniometers attached to the joint in question with the exercise being performed through a prescribed number of sets and repetitions in each set and a prescribed range of motion so as to enable the clear monitoring of the rehabilitation process. Thus, in the above examples, the physical or occupational therapist might set up the device so as to cause the patient to flex the joint in the desired manner through a range of motion for, for example, 75°, for three sets of ten repetitions each. In setting the machine up in this way, the therapist would program therein three sets of ten repetitions each with a desired range of motion of 75° which numbers would be displayed on the displays 171, 173 and 175 shown in FIG. 11. The device 150 has incorporated therein an audible signal such as a buzzer or beeping device (not shown). The audible device is activated only when the patient moves the joint through at least the prescribed range of motion or is unable to move the joint through the prescribed range of motion during a prescribed period of time, for example, 30 seconds. For example, if the prescribed range of motion is to be 75° and the patient only moves the joint through a 70° range of motion, the audible device will not immediately sound and the present invention will not give an indication that a repetition has been accomplished. If, for example, 30 seconds have transpired and the next repetition has not been completed during that time period, the signal will continuously sound to alert the therapist who can tell from the display that the prescribed sets and reps have not been completed indicating either an excessively high range of motion goal has been set or that the patient is fatigued. However, when the patient has actually moved the joint through the range of motion of at least 75° within 30 seconds, the audible device will sound, and the display 175 will increase in number by one, indicating that a repetition has been accomplished. When the display 175 is at one less than the total number of repetitions in a set and a repetition is accomplished, if more than one set is left to be accomplished, the display 173 will add to its number and the display 175 will then display 0 in the repetition column in preparation for the next set of reps which are to be accomplished. When all the sets and repetitions have been accomplished, the audible device will continuously sound to let the patient and therapist know that the exercise regime has been accomplished. Thus, in successive treatments, the range of motion may be gradually increased and the sets and repetitions may be altered as desired until such time as the rehabilitation is complete. Thus, a plateau may be reached wherein further range of motion may not be able to be attained by the patient as may be discovered through the patient's failure to cause the audible device to sound at a set range of motion. Thus, the therapist will know that the maximum attainable range of motion has been attained or that other exercise regimens may be required.

Again, with reference to FIG. 4, it is seen that when the mode switch 181 is turned to the range of motion mode, the buttons 153, 157, 161 and 169 may be pressed as desired so as to comprise a command to the computer to receive data of one of four kinds as follows: (1) data indicating the performance of one measurement of one inputted joint; (2) data indicative of the performance of plural measurements of one inputted joint which is accomplished through pressing of a single button 153 more than once; (3) data indicative of the performance of measurements of a predetermined sequence of joints and motion; or (4) performance of measurements of an inputted sequence of joints. The third mentioned command is normally accomplished through software programming and depression of an appropriate button in the block of buttons 159 relating to examination control. For example, the software may be programmed so that measurement of a predetermined sequence of ranges of motion of the joints may be accomplished in accordance with a book entitled "The American Medical Association Impairment Rating Book". This book has been devised by the American Medical Association so as to enable a physician to determine the total impairment of an individual based upon measurements of the ranges of motion of the various joints of the body. The book is laid out in a predetermined sequence of examination and indicates in each range of motion test what the optimum range of motion should be for that particular joint and movement thereof. Thus, software has been devised for utilization in conjunction with the present invention which will allow the physician to perform an examination in precisely the same order as set forth in the above described American Medical Association book and which will enable the present invention to print out the results of that examination in the exact sequence of examination. Further, the above described American Medical Association book utilizes a formula to calculate the total impairment based upon comparisons of each actual range of motion as compaired to the optimal range of motion. The software of the present invention has been also programmed so that at the end of the examination, this figure indicative of the total impairment is also printed on the paper roll by the printer 129.

With reference back to FIG. 5, if one of the four above described commands has been received, the computer waits to receive inputs indicative of the completion of the appropriate measurements and displays these inputs while storing them in the memory. If plural sequential measurements have not been requested, a print out of the measurements made is done and the procedure is completed. If, however, plural sequential measurements have been requested either in a predetermined sequence or an inputted sequence, all further inputs are sequentially received, displayed and stored and thereafter are printed out.

If the mode switch 181 has been shifted to the biofeedback mode, the computer awaits receipt of information indicative that the joint to be exercised has been inputted, that inputs have been received as to the particular motion of the joint which is to be exercised, the sets and repetitions thereof and the desired range of motion. Then, the micro-computer awaits receipt of signals indicating that exercising is taking place. If each repetition achieves the set range of motion, each repetition is indicated as completed by a visual and audible indicator with the audible indicator being the beep or buzzer described hereinabove and the visual indication being the reduction of the sets and reps as appropriate in the displays 173 and 175. If the set range of motion is not achieved by the patient, the computer waits until such time as the range of motion is achieved before indicating that a repetition has been accomplished. In this situation, if the patient never achieves the set range of motion, after a prescribed period of time, the computer may indicate the failure to achieve the set range of motion within the prescribed period by an audible indication. After the preset sets and repetitions are completed, this is visually indicated in the displays 173 and 175 and a print out is made having printed thereon the patient's name and identification number, the joint which has been exercised, and the joint motion thereof, the sets and repetitions accomplished and the range of motion accomplished. At this point, another exercise of either this joint or another joint may be accomplished through resetting the device with the reset button 179 and inputting new information.

Thus, an invention has been disclosed hereinabove which overcomes all of the deficiencies in the prior art and accomplishes all the objects set forth hereinabove. It is understood that various modifications, changes and alterations in the teachings of the present invention may be made by those skilled in the art without departing from the intended scope and spirit thereof. Accordingly, it is to be stressed that it is intended that the present invention only be limited by the terms of the following claims.

We claim:

1. A device for measuring and displaying the range of motion of any of the joints of the body during the examination thereof comprising:
   (a) sensor means attachable to any of said joints for sensing said range of motion and responsive thereto producing a signal indicative of said range of motion;
   (b) control means electrically connected to said sensor means for receiving said signal and, therefrom, calculating said range of motion;
   (c) display means controlled by said control means for displaying said range of motion as calculated by said control means;
   (d) said sensor means including calibration means for calibrating said sensor means prior to measuring said range of motion; and
   (e) said control means including mode switching means switchable between a first mode enabling said device to measure and display the range of motion of one or more joints in a predetermined fashion and a second mode enabling said device to monitor the exercising of a particular joint for a predetermined number of repetitions, each repetition comprising the movement of said particular joint through a predetermined minimum range of motion, said control means sensing each repetition and activating indicating means responsive to successful completion of each said repetition.

2. The invention of claim 1, wherein said sensor means comprises an electronic goniometer including:
   (a) a casing having an interior peripheral wall of substantially circular configuration;
   (b) a resistor film fixedly mounted to said peripheral wall and extending circumferentially over a major portion thereof;
   (c) a pendulum rotatably mounted with respect to said casing at a pivot axis and having a weight at an end thereof remote from said pivot axis and swinging in closely spaced relation to said resistor film;
   (d) a first contact connected to said resistor film and a second contact connected to said weight and engaging said resistor film whereby swinging movement of said pendulum varies the electrical resistance across said contacts.

3. The invention of claim 2, including a plurality of said electronic goniometers each connectable to a distinct body joint and sending a signal to said control means indicative of the range of motion of said distinct body joint, said control means being programmed to receive signals from said electronic goniometers and therefrom to calculate the ranges of motion of said distinct body joints with respect to one another.

4. The invention of claim 2, wherein said resistor film comprises a highly mechanically oriented carbon material with highly resistance sensitive unidirectional crystals.

5. The invention of claim 2, further including freeze means connected to said control means for freezing said signals, said freeze means being selectively actuable to freeze said signal at its value at the instant of actuation of said freeze means.

6. The invention of claim 5, wherein said calibration means, said freeze means and said display means form an integral part of said electronic goniometer.

7. The invention of claim 2, wherein said pendulum is rotatably mounted with respect to said casing via a bearing which enables said pendulum to freely swing when said casing is tilted up to 70° in a direction perpendicular to the direction of swing of said pendulum.

8. The invention of claim 1, further including freeze means connected to said control means for freezing said signal, said freeze means being selectively actuable to freeze said signal at its value at the instant of actuation of said freeze means.

9. The invention of claim 1, wherein said display means comprises a series of light emitting diodes arranged to display numerical values as well as indications of relative displacements of joints.

10. The invention of claim 9, wherein said display means further includes a printer connected to said control means for printing displayed information onto a roll of paper associated therewith.

11. The invention of claim 1, further including storage means connected to said control means for storing data related to said signal and for storing data related to a plurality of such signals sequentially received by said control means.

12. The invention of claim 1, further including input means connected to said control means for inputting to said control means information concerning a particular sequence of measurements to be undertaken by said device.

13. The invention of claim 12, wherein said input means includes:
   (a) a first set of buttons each of which when activated inputs to said control means information identifying a particular joint or sequence of joints the range of motion of which will be measured;
   (b) a second set of buttons each of which when activated inputs to said control means information identifying a particular direction of movement of said joint or sequence of joints; and
   (c) a third set of buttons each of which when activated inputs to said control means further information concerning said examination.

14. The invention of claim 13, wherein said further information includes information as to left or right joint, and as to whether said examination will be passive or active.

15. The invention of claim 1, wherein said control means has electrically connected thereto a computer program consisting of a detachable software package.

16. The invention of claim 15, wherein said program includes means for programming said control means in said second mode to activate an audible or visual signal when a user thereof is unable to move a particular joint through a prescribed range of motion during a prescribed time period.

17. The invention of claim 15, wherein said program includes means for programming said control means in said first mode to receive commands enabling said device to measure the range of motion of a single joint in a single direction of motion once.

18. The invention of claim 15, wherein said program includes means for programming said control means in said first mode to receive commands enabling said device to measure the range of motion of a single joint in a single direction of motion a predetermined plurality of times.

19. The invention of claim 15, wherein said program includes means for programming said control means in said first mode to receive commands enabling said device to measure the ranges of motion of a plurality of joints in predetermined directions of motion in a predetermined sequence.

20. The invention of claim 15, wherein said program includes means for programming said control means in said first mode to receive commands enabling said device to measure the range of motion of a plurality of joints in predetermined directions of motion in an inputted sequence.

21. The invention of claim 15, wherein said program includes means for programming said control means in said first mode to receive signals from a plurality of said sensor means simultaneously.

22. The invention of claim 21, wherein said plurality of sensor means comprises four said sensor means.

23. The invention of claim 1, wherein said repetitions are divded into a plurality of sets, said control means monitoring each repetition and causing said display means to display the number of sets and repetitions remaining in an ongoing basis and updating information displayed by said display means after each repetition.

24. The invention of claim 23, further including printing means for printing a permanent record of sets, repetitions, range of motion achieved and patient identification when said exercising of said particular joint is completed.

* * * * *